(12) United States Patent
Virji et al.

(10) Patent No.: US 9,034,266 B2
(45) Date of Patent: May 19, 2015

(54) POLYANILINE NANOFIBER HYDROGEN SENSORS

(75) Inventors: Shabnam Virji, Yorba Linda, CA (US); Richard B. Kaner, Pacific Palisades, CA (US); Bruce H. Weiller, Santa Monica, CA (US)

(73) Assignees: The Aerospace Corporation, El Segundo, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/196,011

(22) Filed: Aug. 2, 2011

(65) Prior Publication Data

US 2011/0300637 A1 Dec. 8, 2011

Related U.S. Application Data

(62) Division of application No. 11/554,009, filed on Oct. 28, 2006, now abandoned.

(51) Int. Cl.
| | | |
|---|---|---|
| G01N 27/00 | (2006.01) | |
| G01N 27/12 | (2006.01) | |
| B82Y 15/00 | (2011.01) | |
| G01N 33/00 | (2006.01) | |
| G01N 21/00 | (2006.01) | |

(52) U.S. Cl.
CPC .............. *G01N 27/127* (2013.01); *B82Y 15/00* (2013.01); *G01N 27/126* (2013.01); *G01N 33/005* (2013.01)

(58) Field of Classification Search
None
See application file for complete search history.

(56) References Cited

U.S. PATENT DOCUMENTS

| | | | | |
|---|---|---|---|---|
| 2002/0105080 | A1* | 8/2002 | Speakman | 257/749 |
| 2002/0141901 | A1* | 10/2002 | Lewis et al. | 422/82.01 |
| 2003/0109056 | A1* | 6/2003 | Vossmeyer et al. | 436/169 |
| 2004/0074779 | A1* | 4/2004 | Sotzing | 205/414 |
| 2005/0126909 | A1* | 6/2005 | Weiller et al. | 204/418 |
| 2006/0231805 | A1* | 10/2006 | Wang et al. | 252/500 |

* cited by examiner

*Primary Examiner* — Neil N Turk
(74) *Attorney, Agent, or Firm* — Koppel, Patrick, Heybl & Philpott; Michael J. Ram

(57) ABSTRACT

A method for sensing hydrogen includes the use of a transduction device with a sensing layer, and means for measuring a mass and/or conductivity change caused by an interaction of a gas with the sensing layer to provide a measure of an amount of hydrogen in the gas. The sensing layer includes polyaniline nanofiber material.

25 Claims, 14 Drawing Sheets

SEM images of polyaniline nanofibers (left) and a cross section of a conventional polyaniline film (right).

Response of camphorsulfonic acid (CSA) doped polyaniline nanofibers films exposed to 1% $H_2$.

Response of camphorsulfonic acid (CSA) doped polyaniline nanofibers exposed to different hydrogen concentrations. The dashed line is the $H_2$ concentration plotted on right axis.

Response curve of camphorsulfonic acid (CSA) doped polyaniline nanofibers to different hydrogen concentrations plotted as $-\Delta R/R_0$.

Response of camphorsulfonic acid (CSA) doped polyaniline nanofibers exposed to 1% $H_2$ in the absence of humidity (labeled "A", left axis), in the presence of 50% relative humidity (labeled "B", right axis), and back to a dry environment (labeled "C", left axis).

Response of camphorsulfonic acid (CSA) doped polyaniline nanofibers exposed to 1% $H_2$ in the presence (labeled "A") and absence of 20 % oxygen (labeled "B").

Response of camphorsulfonic acid (CSA) doped polyaniline nanofibers exposed to 1% $H_2$ (labeled "A") and 1% $D_2$ (labeled "B").

QCM frequency response of camphorsulfonic acid (CSA) doped polyaniline nanofibers to 1% $H_2$ (labeled "A") and 1% $D_2$ (labeled "B").

Response of camphorsulfonic acid (CSA) doped polyaniline nanofibers (labeled "A", left axis) and conventional polyaniline (labeled "B", right axis) films exposed to 1% $H_2$.

Camphorsulfonic acid (CSA) doped polyaniline nanofibers deposited on gold electrodes (---) and platinum electrodes (—) exposed to 1 percent hydrogen in a dry environment.

Camphorsulfonic acid (CSA) doped conventional polyaniline deposited on gold electrodes (---) and platinum electrodes (—) exposed to 1 percent hydrogen in a dry environment.

IV curves of camphorsulfonic acid (CSA) doped polyaniline nanofibers deposited on a) gold electrodes and b) platinum electrodes before (---) and after (—) exposure to 1 percent hydrogen in a dry environment.

IV curves of camphorsulfonic acid (CSA) doped conventional polyaniline deposited on a) gold electrodes and b) platinum electrodes before (---) and after (—) exposure to 1 percent hydrogen in a dry environment.

POLYANILINE NANOFIBER HYDROGEN SENSORS

This application is a Divisional of application Ser. No. 11/554,009, filed Oct. 28, 2006 now abandoned.

TECHNICAL FIELD

The invention relates generally to sensors and, in particular, to sensors incorporating polyaniline nanofibers.

BACKGROUND ART

The primary physical hazards associated with hydrogen gas are its flammability and explosiveness. This is because hydrogen can form flammable mixtures in air over a wide range of concentrations (4% to 75%), and very low energy is needed to ignite hydrogen-air mixtures. Hence sensors are required to detect hydrogen leaks to warn of explosion hazards.

Existing sensors for detecting hydrogen use palladium metal (Zuttel, A.; Nutzenadel, Ch.; Schmid, G.; Chartouni, D.; Schlapbach, L. *J. Alloys Compd.* 1999, 472-475; Watari, N.; Ohnish, S.; Ishi, T. *J. Phys. Condens. Matter,* 2000, 12, 6799-6823) and palladium alloys (Hughes, R. C.; Schubert, W. K. *J. Appl. Phys.* 1992, 71, 542-544.) The disadvantage of using pure palladium based sensors is the irreversible phase change associated with exposure of palladium to hydrogen. This phase change causes thin films to delaminate from the sensor surface. The advantage of using palladium alloys, especially the Pd/Ni alloy, is the suppression of the phase transition. The response of the alloy materials is also very fast and reversible. The disadvantage of these films is that they require elevated temperatures to work well and are inhibited by oxygen.

Conducting polymers such as polyaniline (Huang, J.; Virji, S.; Weiller, B. H.; Kaner, R. B. *Chem. Eur. J.* 2004, 10, 1314-1319), polypyrrole (Ratcliffe, N. M. *Anal. Chim. Acta* 1990, 239, 257-262), and polythiophene (Ellis, D. L.; Zakin, M. R.; Bernstein, L. S.; Rubner, M. F. *Anal. Chem.* 1996, 68, 817-822) have been widely used to develop fast and efficient chemical sensors. Conducting polymers are highly desirable because they are inexpensive and easy to synthesize. Of the conducting polymer sensors, polyaniline appears to be the most widely studied due to its ease of synthesis and stability in air.

Janata, et al. (in Domansky, K.; Baldwin, D. L.; Grate, J. W.; Hall, T. B.; Josowicz, M.; Janata, *J. Anal. Chem.* 1998, 70, 473-481) have shown that a field effect transistor with 2 layers, palladium and polyaniline can be used as a good sensor for hydrogen. These sensors operate at 90° C. and display fast response times. Recently, it has been reported that conducting polymers may have some ability to store hydrogen. Cho, S. J.; Song, K. S.; Kim, J. W.; Kim, T. H.; Choo, K. *Fuel Chem. Div. Prepr.* 2002, 47, 790-791; Panella, B.; Kossykh, L.; Dettlaff-Weglikowska, U.; Hirscher, M.; Zerbi, G.; Roth, S. *Synth. Met.* 2005, 151, 208-210.

It would be useful to be able to provide a sensor that is not subject to the response limitations of conventional polyaniline. It would also be helpful to be able to provide a room temperature hydrogen sensor.

SUMMARY OF THE INVENTION

The present invention generally involves sensor devices with transduction elements that interact with hydrogen. Embodiments described herein include hydrogen sensor devices incorporating polyaniline microfiber material.

In an example embodiment, an apparatus for sensing hydrogen includes a transduction device with a sensing layer that includes polyaniline nanofiber material, and means (e.g., circuitry) for measuring a mass and/or conductivity change caused by an interaction of a gas with the sensing layer to provide a measure of an amount of hydrogen in the gas.

In an example embodiment, a method for sensing hydrogen includes introducing a gas into a sensor that includes electrodes and a polyaniline nanofiber material between the electrodes, the polyaniline nanofiber material being doped, and measuring, at the electrodes, a conductivity change of the polyaniline nanofiber material to provide a measure of an amount of hydrogen in the gas.

In an example embodiment, a method for sensing hydrogen includes introducing a gas into a mass sensor with a sensing layer that includes polyaniline nanofiber material, and measuring a mass change caused by an interaction of the gas with the sensing layer to provide a measure of an amount of hydrogen in the gas.

DISCLOSURE OF INVENTION

Figure 1:
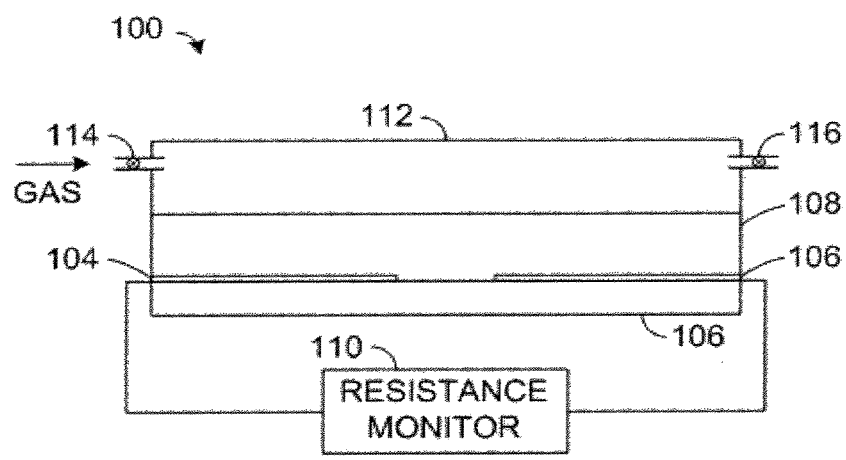
FIG. 1 illustrates an example embodiment of a polyaniline chemiresistor (or sensor).

Referring to FIG. 1, in an example embodiment, a polyaniline chemiresistor (or sensor) 100 includes a substrate 102, electrodes 104 and 106, a polyaniline film (or sensing layer) 108, and a resistance monitor 110 to monitor current flowing through the resistor. The sensor 100 also includes a chamber (or flow cell) 112 with inlet and outlet ports 114 and 116, which are controlled in a conventional fashion to introduce a gas into the sensor 100. The electrodes 104 and 106 can be a metal such as gold or platinum. In an example embodiment, the polyaniline film 108 includes a polyaniline nanofiber material (discussed below).

Figure 2:
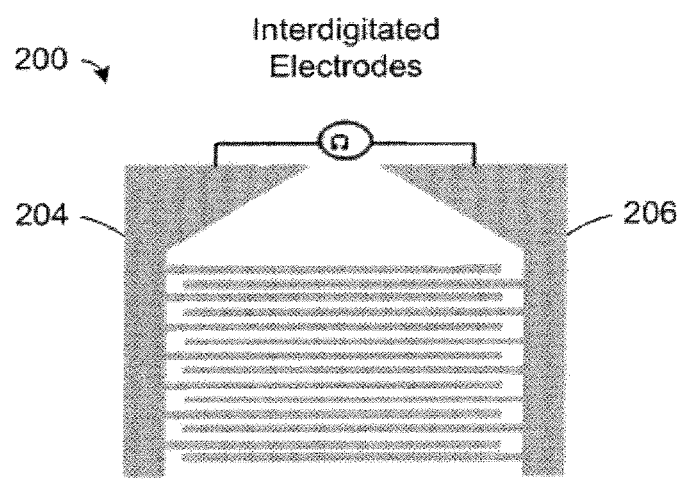
FIG. 2 illustrates an example configuration of interdigitated electrodes for a chemical sensor array.

FIG. 2 illustrates an example configuration of an electrode structure 200 for a chemical sensor array. The electrode structure 200 includes electrodes 204 and 206, which are interdigitated as shown. A resistance monitor 210 is electrically connected between the electrodes 204 and 206.

Other embodiments (primarily) involve measurement of mass change (e.g., quartz crystal microbalance (QCM) or surface acoustic wave (SAW) gas sensor technologies), in lieu of changes in conductivity.

Figure 3:
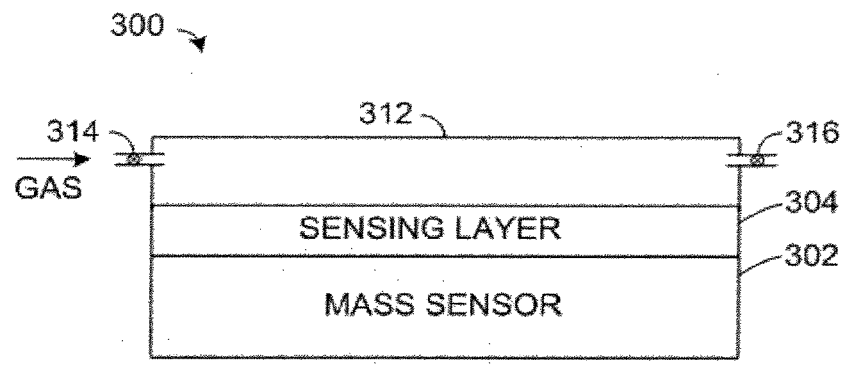
FIG. 3 illustrates an example embodiment of a sensor that measures mass change.

Referring to FIG. 3, in an example embodiment, a sensor 300 includes a mass sensor 302 with a sensing layer 304. The sensor 300 also includes a chamber (or flow cell) 312 with inlet and outlet ports 314 and 316, which are controlled in a conventional fashion to introduce a gas into the sensor 300. By way of example, the mass sensor 302 can be a surface acoustic wave (SAW) device or a quartz crystal microbalance (QCM) device. In an example embodiment, the sensing layer 304 includes a polyaniline nanofiber material (discussed below).

The mass sensor 302 can be a layered SAW transducer, which has higher sensitivity than its nonlayered counterpart. In an example embodiment, polyaniline nanofibers are deposited onto the active area of a SAW device as a sensing layer. In a SAW device, the change in electrical conductivity perturbs the velocity of the propagating acoustic wave due to piezoelectric effects. The deviations in velocity are monitored by measuring the changes in frequency of the sensing device. This change in frequency is directly proportional to the amount of a specific gas present in the environment, resulting in a quantitative determination of the presence of gas and its concentration. For hydrogen sensing applications, a polyaniline nanofiber sensitive layer can be formed on the layered SAW transducer.

Hydrogen causes a reversible decrease in the resistance of a thin film of camphorsulfonic acid doped polyaniline nanofibers. For a 1% mixture of hydrogen in nitrogen, a 3% decrease in resistance is observed ($\Delta R/R=-3\%$). The hydrogen response is completely suppressed in the presence of humidity. In contrast, oxygen does not inhibit the hydrogen response. A deuterium isotope effect on the sensor response is observed in which hydrogen gives a larger response than deuterium: $(\Delta R/R)_H/(\Delta R/R)_D=4.1\pm0.4$. Mass sensors using nanofiber films on a quartz crystal microbalance also showed a comparable deuterium isotope effect: $\Delta m_H/\Delta m_D=2.3\pm0.2$. The resistance change of polyaniline nanofibers is about an order of magnitude greater than conventional polyaniline consistent with a porous, high surface area nanofibrillar film structure that allows for better gas diffusion into the film. A plausible mechanism involves hydrogen bonding to the amine nitrogen along the polyaniline backbone and subsequent dissociation. The inhibitory effect of humidity is consistent with a stronger interaction of water with the polyaniline active sites that bind to hydrogen. These data clearly demonstrate a significant interaction of hydrogen with doped polyaniline and may be relevant to recent claims of hydrogen storage by polyaniline.

Experimental Comparison

Figure 4:
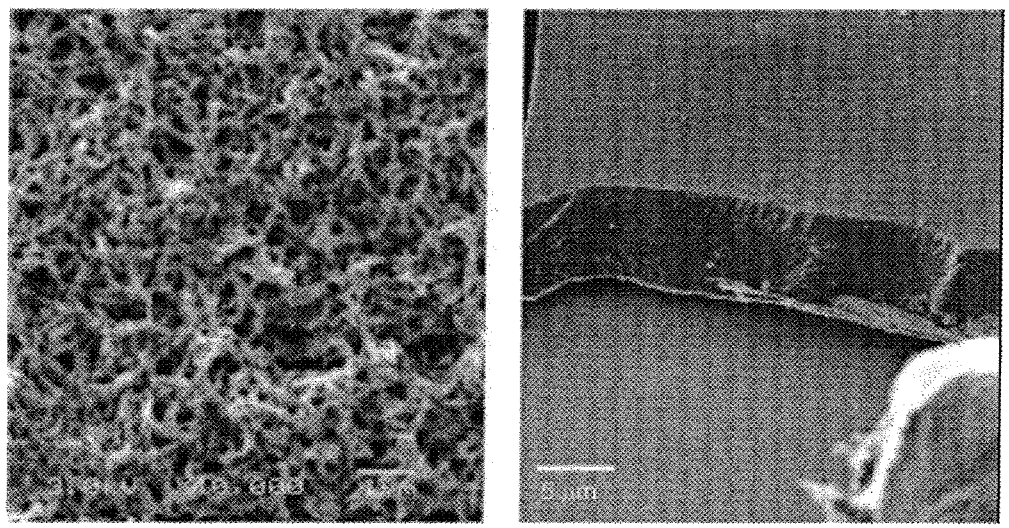
FIG. 4 shows scanning electron micrograph (SEM) images of polyaniline nanofibers (left) and a cross section of a conventional polyaniline film (right).

Polyaniline nanofibers were synthesized using an aqueous, one-pot, rapidly-mixed process and purified by centrifugation. The nanofibers were dried and subsequently redispersed in water to form a final concentration of 1 g/L. This solution was then deposited on sensor array substrates with an airbrush to form a thin film. Conventional polyaniline was chemically synthesized from aniline by oxidative polymerization using ammonium peroxydisulfate in an acidic media. Reacting the salt form with base produces the emeraldine base form of polyaniline. Huang, W.-S.; Humphrey, B. D.; MacDiamid, A. G. *J. Chem. Soc, Faraday Trans.* 1986, 82, 2385-2400 (incorporated herein by reference). Conventional polyaniline solutions were made by dissolving polyaniline in hexafluoroisopropanol (HFIP, 2 mg/mL). FIG. 4 shows scanning electron micrograph (SEM) images of polyaniline nanofibers (left) and a cross section of a conventional polyaniline film (right).

Interdigitated electrode sensor substrates were fabricated using standard photolithographic methods. In an example embodiment, the array sensor includes 6 separate interdigitated electrode sensors fabricated on one substrate using standard photolithographic methods. In an example embodiment, the electrode geometry includes 50 pairs of fingers, each finger having dimensions of 10 µm×3200 µm×0.18 µm (width×length×height) and a 10 µm gap between fingers. In an example embodiment, camphorsulfonic acid (CSA) doped polyaniline nanofibers were deposited onto the sensor array substrates with an airbrush using aqueous nanofiber suspensions. The polyaniline nanofibers can be doped with other dopants such as sulfuric acid ($H_2SO_4$), nitric acid ($HNO_3$), and polymeric acid dopants, e.g., polystyrenesulfonic acid (PSSA) and polyacrylic acid (PAA). The polyaniline nanofibers can also be modified ("decorated") with metal nanoparticles, such as gold (Au), silver (Ag), platinum (Pt) and palladium (Pd). Acid doping of polyaniline nanofiber material with these acids also results in a polyaniline material that shows an increase monotonically with hydrogen concentration.

Certified gas mixtures of 10% hydrogen ($H_2$) and 10% deuterium ($D_2$) in nitrogen (Scott Specialty Gases, Inc.) were diluted with nitrogen using calibrated mass flow controllers. Mass flow controllers were used to meter separate flows of nitrogen buffer gas and the calibrated gas mixture. The gas flow experiments were performed using either 0% or 50% relative humidity in the final nitrogen gas flow. The humidity was generated using a bubbler and measured in the nitrogen flow with a humidity sensor (Vaisala). Oxygen inhibition experiments were performed using the ratio of the flows to give a known concentration (20%) of oxygen (Air Products and Chemicals, Inc.) in the gas flow.

Electrical resistances (DC) were measured with a programmable electrometer (Keithley 2001). Mass flow controllers were controlled with a MKS 247 4-channel readout. All instruments were controlled and read by computer using a GPIB interface and LabView software. Quartz crystal microbalance (QCM) measurements were carried out using a standard 6 MHz crystal monitor (Sycon) mounted in a flow cell. QCM crystals were coated in the same way as for the sensors described above.

Results

Hydrogen Response

Figure 5:
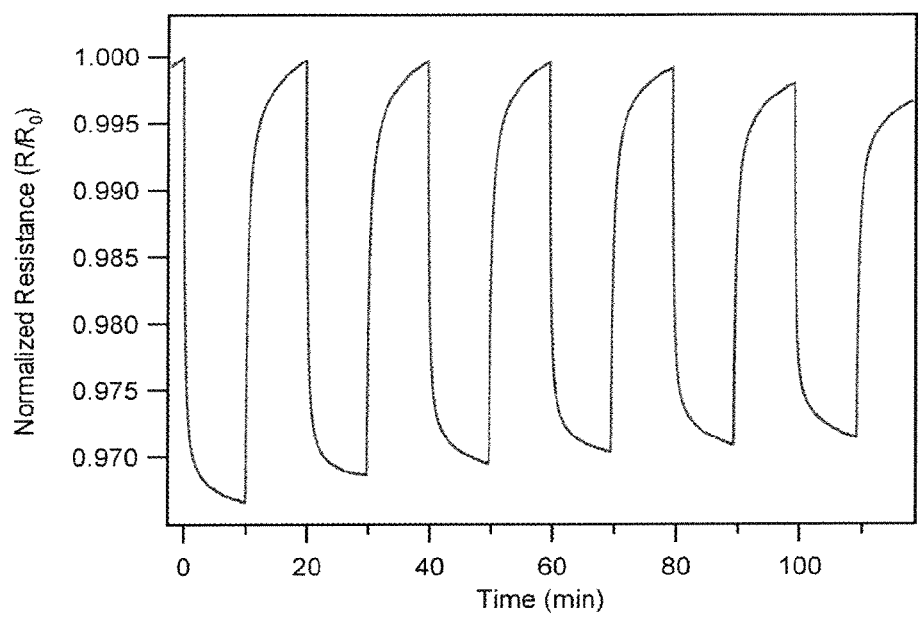
FIG. 5 shows a response of camphorsulfonic acid (CSA) doped polyaniline nanofibers films exposed to 1% $H_2$.

Upon exposure to a 1% mixture of hydrogen in nitrogen, camphorsulfonic acid (CSA) doped polyaniline films show a 3% decrease in resistance at room temperature, $\Delta R/R_0 = -3\%$ (FIG. 5). This response is reversible. However, dedoped polyaniline nanofiber films do not appear to show any response to hydrogen.

Figure 6:
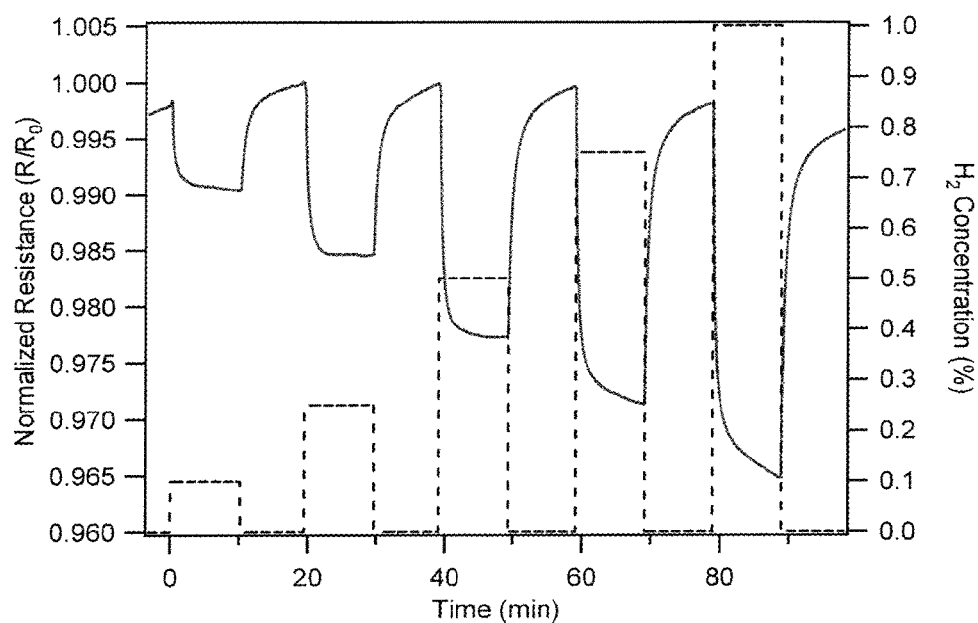
FIG. 6 shows a response of camphorsulfonic acid (CSA) doped polyaniline nanofibers exposed to different hydrogen concentrations. The dashed line is the $H_2$ concentration plotted on right axis.
Figure 7:
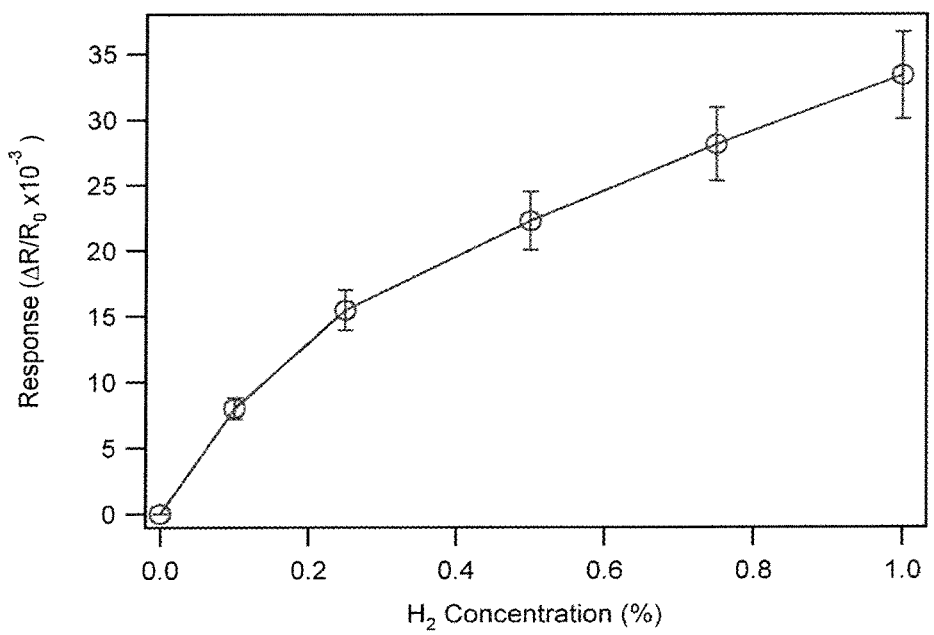
FIG. 7 shows a response curve of camphorsulfonic acid (CSA) doped polyaniline nanofibers to different hydrogen concentrations plotted as $-\Delta R/R_0$.

FIG. 6 shows that the response varies with the concentration of hydrogen. FIG. 7 plots the response ($\Delta R/R_0$) curve associated with these concentrations. The response is reversible (FIG. 6) and increases with concentration over this range. As can be seen from FIG. 7, the response varies monotonically with concentration with the incremental change in response falling off at higher levels. At even higher concentrations (5 to 10%), the hydrogen response completely saturates and the sensor is purged with nitrogen for several hours to regenerate the response.

Humidity Effect

Figure 8:
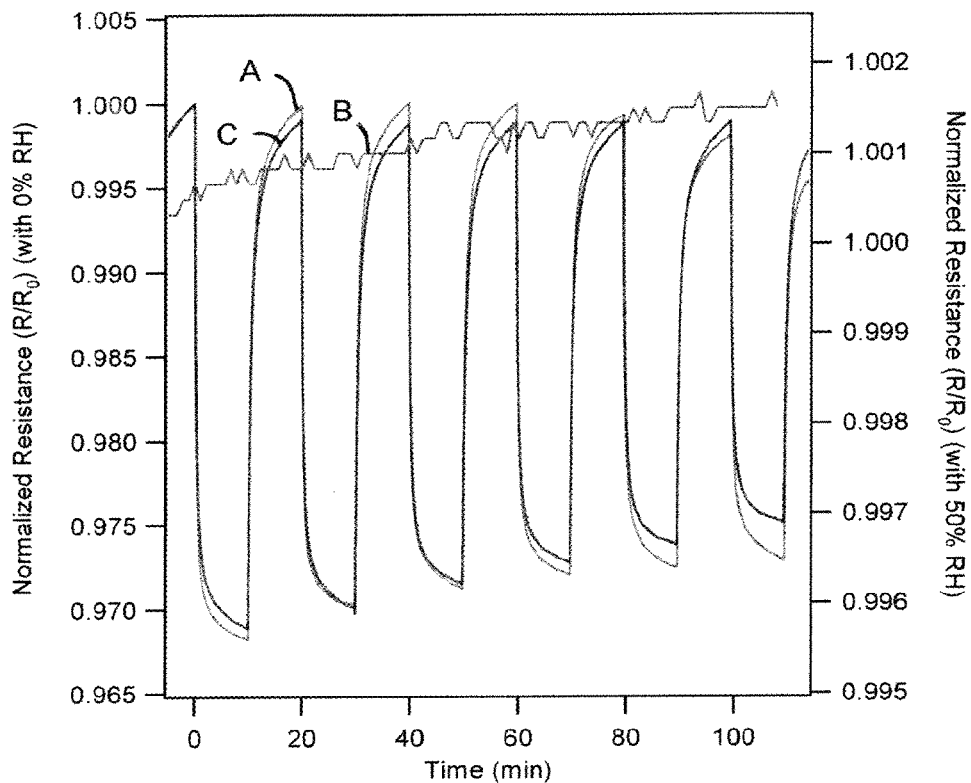
FIG. 8 shows a response of camphorsulfonic acid (CSA) doped polyaniline nanofibers exposed to 1% $H_2$ in the absence of humidity (labeled "A", left axis), in the presence of 50% relative humidity (labeled "B", right axis), and back to a dry environment (labeled "C", left axis).

FIG. 8 shows the response of camphorsulfonic acid doped polyaniline nanofibers exposed to 1% hydrogen in the absence and presence of humidity. The left axis is the normalized resistance ($R/R_0$) and the bottom axis is time. It appears that in the presence of humidity there is essentially no response to hydrogen especially when compared to a dry environment. Water is known to reversibly bind to polyaniline making it more conducting (see, Angelopoulos, M.; Ray, A.; MacDiamid, A. G.; Epstein, A. *J. Synth. Met.* 1987, 21, 21-30; MacDiamid, A. G.; Epstein, A. *J. Faraday Disc. Chem. Soc.* 1989, 88, 317-332; Lubentsov, B. Z.; Timofeeva, O. N.; Khidekel, M. L. *Synth. Met.* 1991, 45, 235-240) and this may interfere with the hydrogen interaction with polyaniline.

After exposure to a humid environment, these same films were then dried in nitrogen and re-exposed to hydrogen. After drying for a short period of time (~1.5 h), the films showed a resistance change that was smaller than the resistance change in a completely dry environment. These films were therefore not sufficiently dry and, as a result, the residual water remaining in the film affected the response of the polyaniline to hydrogen. However, once these films were fully dried by exposure to dry nitrogen overnight, subsequent exposure to hydrogen regenerated the original response. This shows that even a small amount of water left in the film can affect its response to hydrogen.

Oxygen Effect

Figure 9:
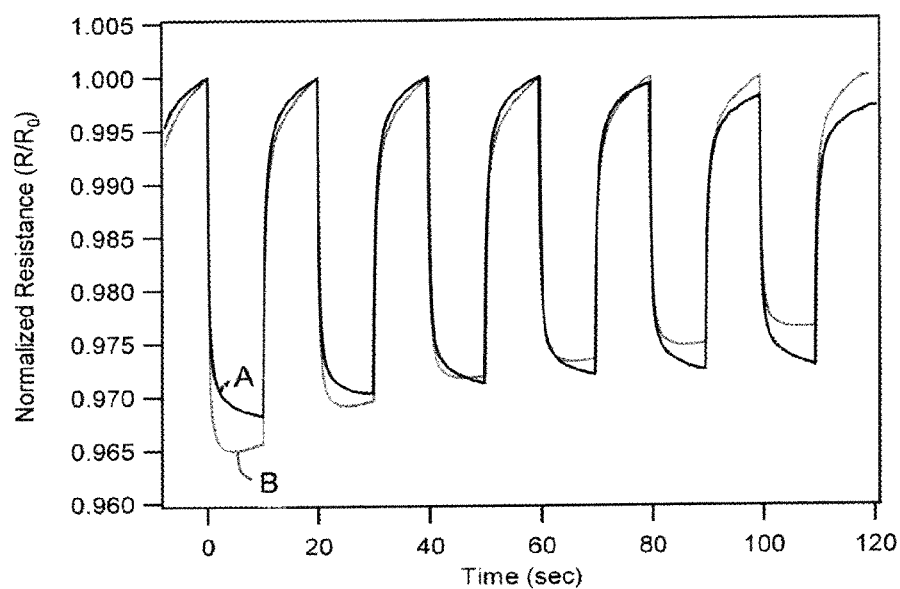
FIG. 9 shows a response of camphorsulfonic acid (CSA) doped polyaniline nanofibers exposed to 1% $H_2$ in the presence (labeled "A") and absence of 20% oxygen (labeled "B").

Oxygen has no significant effect on the response of the nanofibers to hydrogen. FIG. 9 shows the response to hydrogen in the presence and absence of oxygen at normal oxygen concentrations (20%). Within experimental error the response is the same and therefore oxygen has no affect on the sensor response. This is unlike many hydrogen sensors, which are strongly inhibited by the presence of oxygen. See, Tournier, G.; Pijolat, C. *Sens. Actuators B* 1999, 61, 43-50; Mather, G. C.; Marques, F. M. B.; Frade, J. R. *J. Eur. Ceram. Soc.* 1999, 19, 887-891.

Isotope Effect

Figure 10:
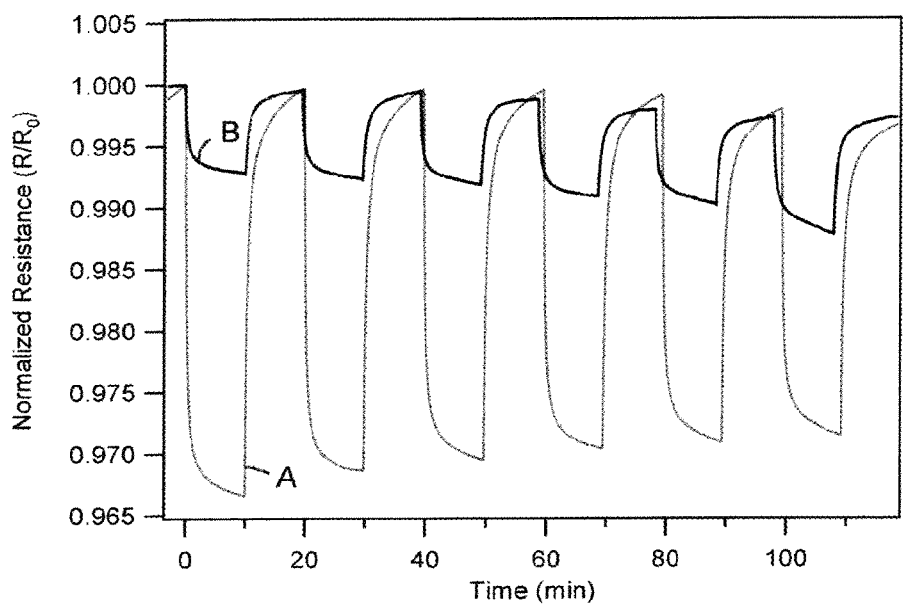
FIG. 10 shows a response of camphorsulfonic acid (CSA) doped polyaniline nanofibers exposed to 1% $H_2$ (labeled "A") and 1% $D_2$ (labeled "B").

The deuterium isotope effect on the sensor response was examined using a calibrated gas mixture of deuterium. FIG. 10 shows the separate responses to mixtures of hydrogen (H) and deuterium (D) at the same concentration (1%). There is a substantial decrease in the signal response for deuterium relative to hydrogen. For the data in FIG. 10, the average hydrogen response is $\Delta R/R = -(3.0 \pm 0.2) \times 10^{-2}$ and for deuterium the average response is $\Delta R/R = -(7.4 \pm 0.3) \times 10^{-3}$. The isotopic ratio of the responses is $(\Delta R/R)_H/(\Delta R/R)_D = 4.1 \pm 0.4$.

Mass Response

Figure 11:
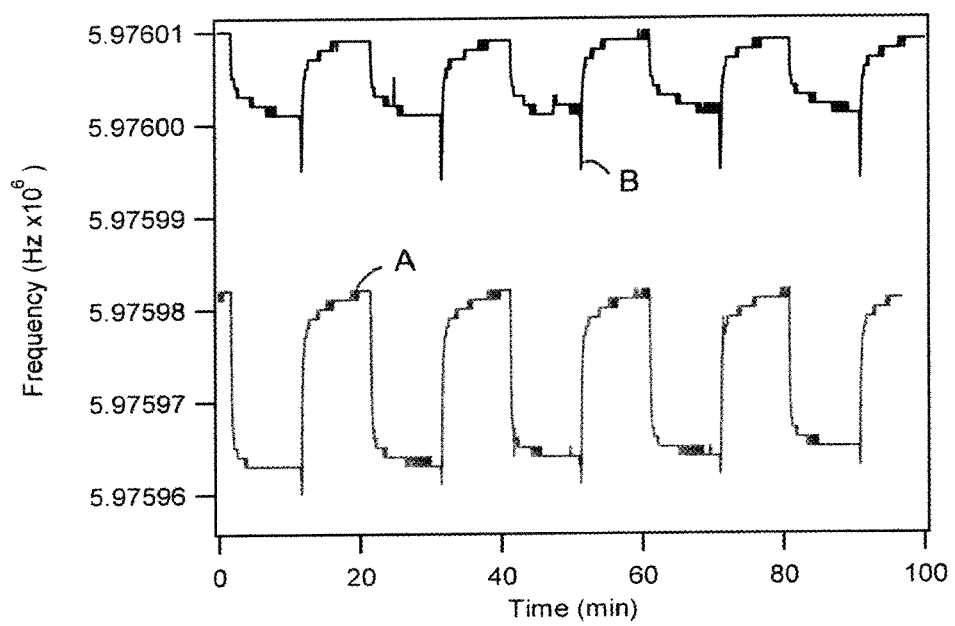
FIG. 11 shows a QCM frequency response of camphorsulfonic acid (CSA) doped polyaniline nanofibers to 1% $H_2$ (labeled "A") and 1% $D_2$ (labeled "B").

The $H_2$ and $D_2$ mass uptake of the nanofibers was measured using a QCM. FIG. 11 shows the response of a QCM crystal coated with polyaniline nanofibers to 1% $H_2$ and to 1% $D_2$. The same coated crystal was used for both experiments. For $H_2$, the average frequency change is $\Delta f = 182 \pm 8$ Hz and for $D_2$ the average frequency change is $\Delta f = 80 \pm 7$ Hz. The isotopic ratio of responses is $\Delta f_H/M_D = \Delta M_H/\Delta M_D = 2.3 \pm 0.2$ assuming the Sauerbray equation ($\Delta f \propto \Delta m$) applies. Using the ratio of molecular weights for $H_2$ and $D_2$, the ratio of mass changes can be converted to a molar isotope effect on the interaction of $H_2$ with polyaniline: $\Delta n_H/\Delta n_D = 4.6 \pm 0.4$.

Conventional vs. Nanofiber Polyaniline

Figure 12:
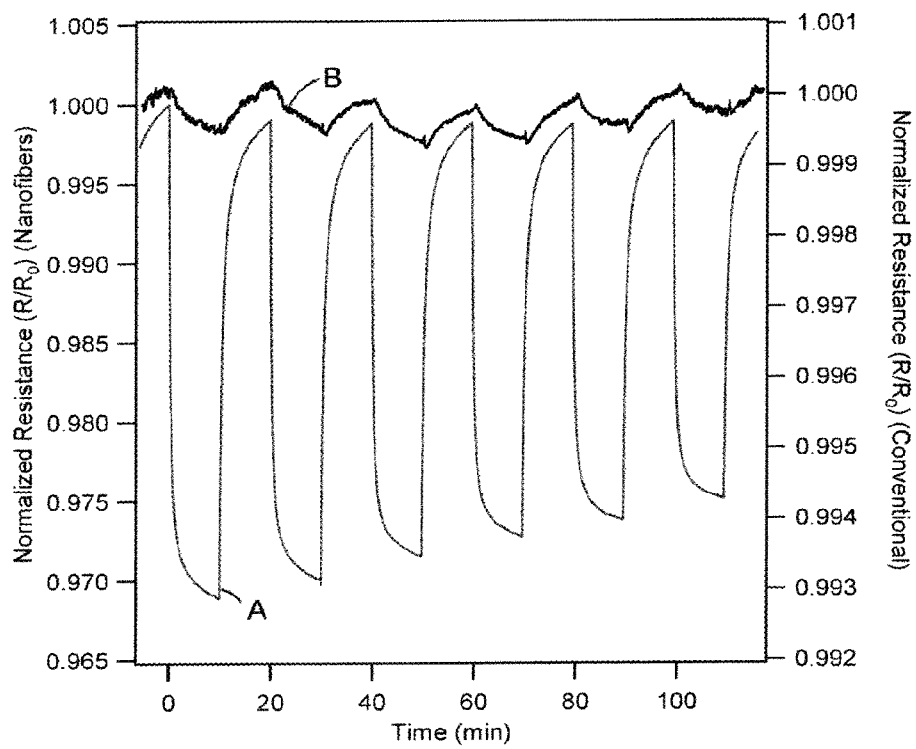
FIG. 12 shows a response of camphorsulfonic acid (CSA) doped polyaniline nanofibers (labeled "A", left axis) and conventional polyaniline (labeled "B", right axis) films exposed to 1% $H_2$.

FIG. 12 compares the response of conventional and nanofiber polyaniline films to 1% hydrogen. The percent change in resistance for the conventional film is about an order of magnitude lower than that for the polyaniline nanofiber film (FIG. 12). The response of conventional polyaniline film is small but real. A control experiment was done with nitrogen alone and it showed no change in resistance upon gas switching indicating that the response is not due to a flow imbalance. It is possible that the observed response from the conventional film is due to changes in gas properties (i.e. thermal conductivity) from the small amount of hydrogen (1%). In any event, the hydrogen response from conventional polyaniline is much smaller than that for the nanofibers.

No pressure or heat was applied to the conventional polyaniline films and this may affect how they respond to hydrogen. The percent change in resistance for the conventional film is an order of magnitude lower than that for the polyaniline nanofiber film (FIG. 12). The improved response of the nanofiber film is consistent with the inventors' other results using nanofibers as sensors. Virji, S.; Huang, J.; Kaner, R. B.; Weiller, B. H. *Nano Lett.* 2004, 4, 491-496 (incorporated herein by reference). As discussed previously, it appears that this is due to the high surface area and faster diffusion into the nanofibers because of their small diameters.

The experiments performed in this work used films that were airbrushed from a water suspension onto a heated substrate, dried under nitrogen overnight at atmospheric pressure, and then exposed to hydrogen at room temperature. When the aqueous nanofiber suspension is drop cast onto the electrodes and simply dried at room temperature, the response is significantly smaller. This may be due to the presence of water in the films.

Discussion

The results can be summarized as follows: 1) a reversible response to hydrogen is observed from doped polyaniline, 2) there is no response from dedoped polyaniline, 3) a strong inhibition by humidity is observed, 4) no inhibition is found with oxygen, 5) a significant deuterium isotope effect is observed, 6) hydrogen mass uptake by QCM measurements confirms a deuterium isotope effect, and 7) there is no significant response from conventional polyaniline films. MacDiamid (in MacDiamid, A. G. "Conducting Polymers as New Materials for Hydrogen Storage" DOE presentation May 2005) has presented a possible mechanism for the interaction of hydrogen with polyaniline and it is reproduced in Scheme I (below) with A⁻ representing any dopant anion. In this scheme, hydrogen interacts with doped polyaniline at the charged amine nitrogen sites. $H_2$ bond dissociation follows with formation of new N—H bonds to the amine nitrogen of the polyaniline chain. Subsequent charge transfer between adjacent amine nitrogens returns the polyaniline back to its polaronic, doped, emeraldine-salt state with a release of hydrogen making this reaction fully reversible.

This mechanism works for the emeraldine salt form of polyaniline but not for the emeraldine base form of polyaniline. The emeraldine base form contains alternate amine and imine nitrogens and is the insulating form of polyaniline. Because it is insulating there is no charge transfer between the nitrogen units on the polymer chain, which would hinder the interaction of hydrogen with the polymer chain. Because hydrogen cannot dissociate and interact with the polyaniline there would be no response to hydrogen expected from dedoped forms of polyaniline. FIG. 5 indicates that there is no response of dedoped polyaniline nanofibers to hydrogen; this is consistent with Scheme I.

As seen from the proposed mechanism in Scheme 1, the first step is hydrogen bonding with polyaniline at the nitrogen atoms of the polyaniline chain. Water could also bind to these same sites. It seems likely that water would have a higher binding affinity to these sites and therefore hydrogen would not be able to displace water. Complete suppression of the hydrogen response in a humid atmosphere is consistent with this mechanism.

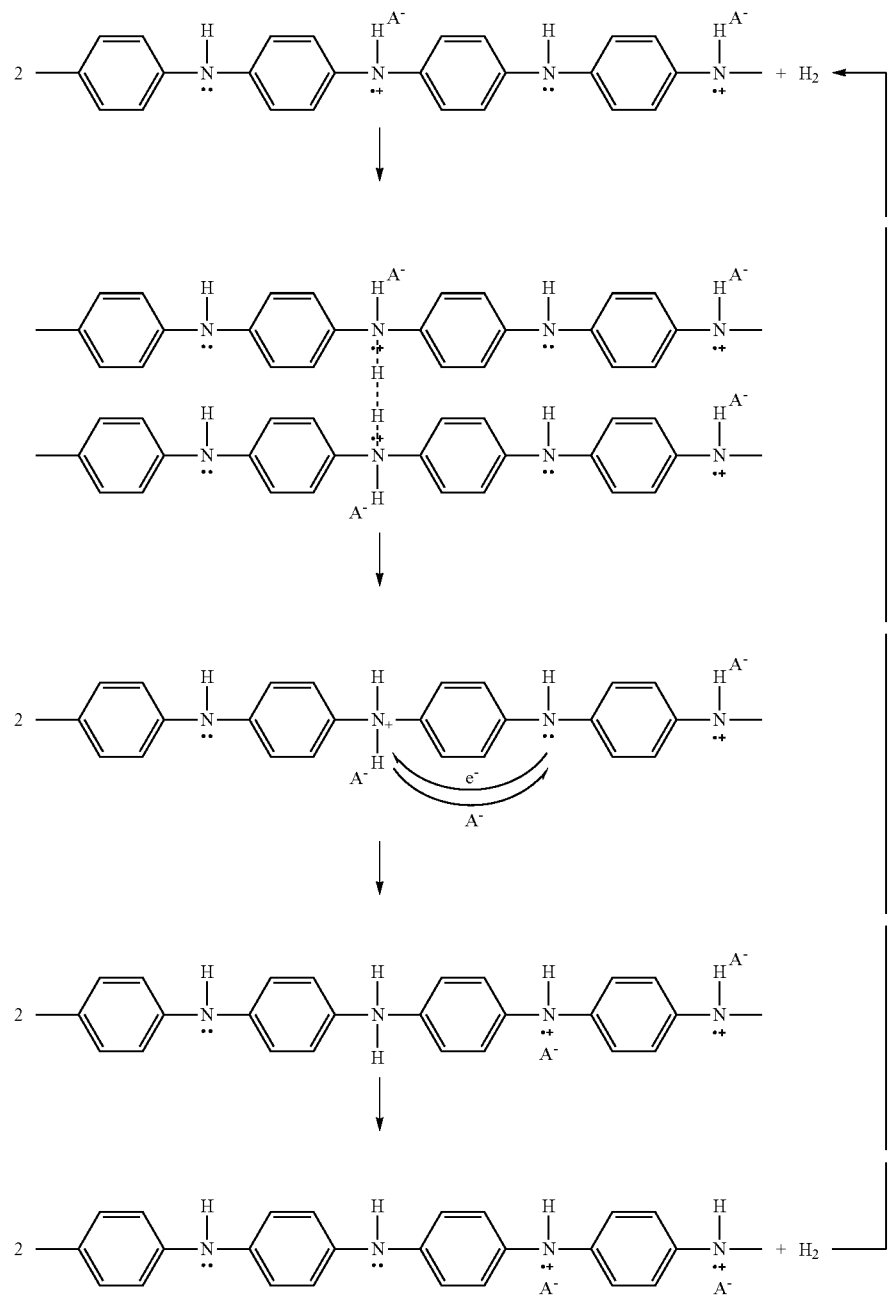

Scheme 1 Possible mechanism for hydrogen interaction with doped polyaniline where A⁻ represents the counteranion.

No inhibition by oxygen on the hydrogen response was observed. This is interesting because with palladium-based sensors, oxygen interacts with the palladium hydride surface to generate water and, as a result, reduces the signal to hydrogen. See, Weiller, B. H.; Barrie, J. D.; Aitchison, K. A.; Chaffee, P. D.; *Mater. Res. Soc. Sym. Proc.* 1995, 360, 535-540. The mechanism in Scheme 1 shows that hydrogen dissociates and binds to the nitrogens along the polyaniline chain. The hydrogen in this case may not react as readily with oxygen as with palladium hydride if a new covalent N—H bond with polyaniline is formed.

A significant isotope effect was observed as measured from the resistance change of the films $(\Delta R/R)_H/(\Delta R/R)_D=4.1\pm0.4$, and from the molar hydrogen uptake as measured by the QCM, $\Delta n_H/\Delta n_D=4.6\pm0.4$. The fact that these values are very similar is somewhat surprising, but could result from a fractional resistance change that is linearly related to the molar uptake of hydrogen over this response range. The fact that the hydrogen response is reversible indicates that the interaction of hydrogen with polyaniline is at equilibrium at room temperature. The isotope effect may be explained as an equilibrium isotope effect caused by the difference in zero point energy. The zero point energy depends inversely on the reduced mass of a vibration, which changes significantly upon deuterium substitution. See, Moore, J. W.; Pearson, R. G. "*Kinetics and Mechanism*" Wiley, New York, 1981, pg. 367-369. This leads to a slightly greater dissociation energy for the heavier isotope. This observation appears to be consistent with the hypothesis made by MacDiamid that hydrogen dissociates and forms new N—H bonds at the amine nitrogens of polyaniline. For this mechanism (Scheme I), an equilibrium isotope effect would be expected due to the difference in bond strengths between the $H_2$ and N—H bonds. The vibrational frequency of $H_2$ is 4155 $cm^{-1}$, whereas a typical N—H vibration is approximately 2700 $cm^{-1}$. Isotopic substitution should have a greater effect on the dissociation of $H_2$ compared to the dissociation of the N—H bond. Therefore, the interaction of $D_2$ with polyaniline is less favored than $H_2$ resulting in a smaller resistance change or mass uptake. While other mechanisms are possible, Scheme I is consistent with all of the data presented above.

An interesting aspect of these results is in relation to recent reports of possible hydrogen storage ability by polyaniline. Cho, et al. (cited above) claimed that conventional, HCl-doped polyaniline can sorb up to 6 wt % hydrogen at a pressure of 90 atm and temperature of 25° C. Prior to interaction with hydrogen, the films were dried under vacuum at 473 K and then at room temperature at a pressure of 0.13 Pa. More recently several groups have attempted to reproduce these results with no success even with doped polyaniline nanofibers. Notwithstanding the prior hydrogen storage studies, it appears from the present results that hydrogen interacts with polyaniline nanofibers. The QCM results appear to provide direct evidence of hydrogen mass uptake by doped polyaniline nanofibers.

Schottky Barriers from Polyaniline Nanofibers as Hydrogen Sensors

For hydrogen sensing using gold electrodes, interaction of hydrogen with polyaniline nanofibers has been observed in which the resistance decreases (conductivity increases) upon exposure to hydrogen gas.

For hydrogen sensing using platinum electrodes instead of gold electrodes, a different response was observed. With these sensors, the observed resistance increases upon hydrogen exposure with a much larger magnitude of response. Current versus voltage curves show that with gold there is a good ohmic response but with platinum the curves are nonlinear indicating that Schottky barriers are formed between the polyaniline nanofibers and platinum. The work function of the polyaniline is likely to be changed upon exposure to hydrogen which changes the contact resistance of the device. The formation of Schottky Barriers indicates the possibility of the creating diodes or field effect devices such as capacitors, field effect transistors and related devices that can be used as very sensitive sensors.

Figure 13:
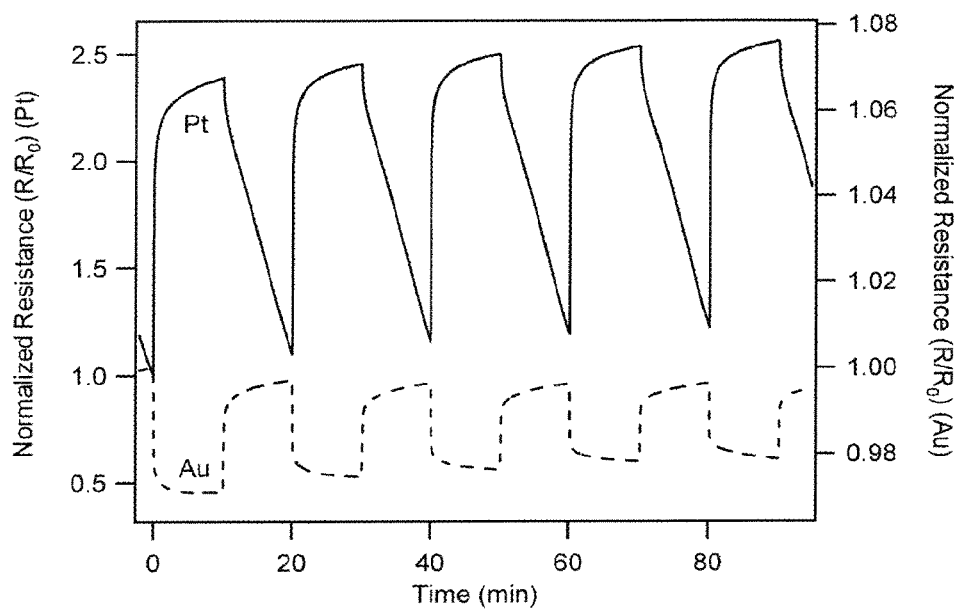
FIG. 13 shows a response of camphorsulfonic acid (CSA) doped polyaniline nanofibers deposited on gold electrodes (- - -) and platinum electrodes (-) exposed to 1 percent hydrogen in a dry environment.
Figure 14:
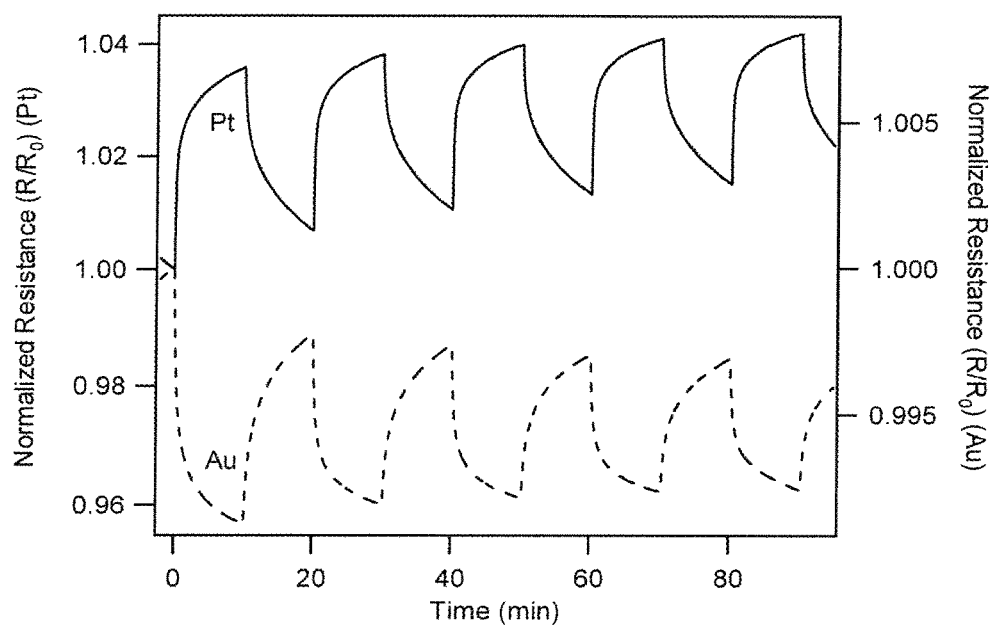
FIG. 14 shows a response of camphorsulfonic acid (CSA) doped conventional polyaniline deposited on gold electrodes ( - - - ) and platinum electrodes (-) exposed to 1 percent hydrogen in a dry environment.

FIG. 13 shows a response of camphorsulfonic acid (CSA) doped polyaniline nanofibers deposited on gold electrodes ( - - - ) and platinum electrodes (-) exposed to 1 percent hydrogen in a dry environment. FIG. 14 shows a response of camphorsulfonic acid (CSA) doped conventional polyaniline deposited on gold electrodes ( - - - ) and platinum electrodes (-) exposed to 1 percent hydrogen in a dry environment. As can be seen, the Normalized Resistance is significantly greater for CSA doped polyaniline nanofibers deposited platinum electrodes, than it is for CSA doped conventional polyaniline deposited platinum electrodes.

Figure 15:
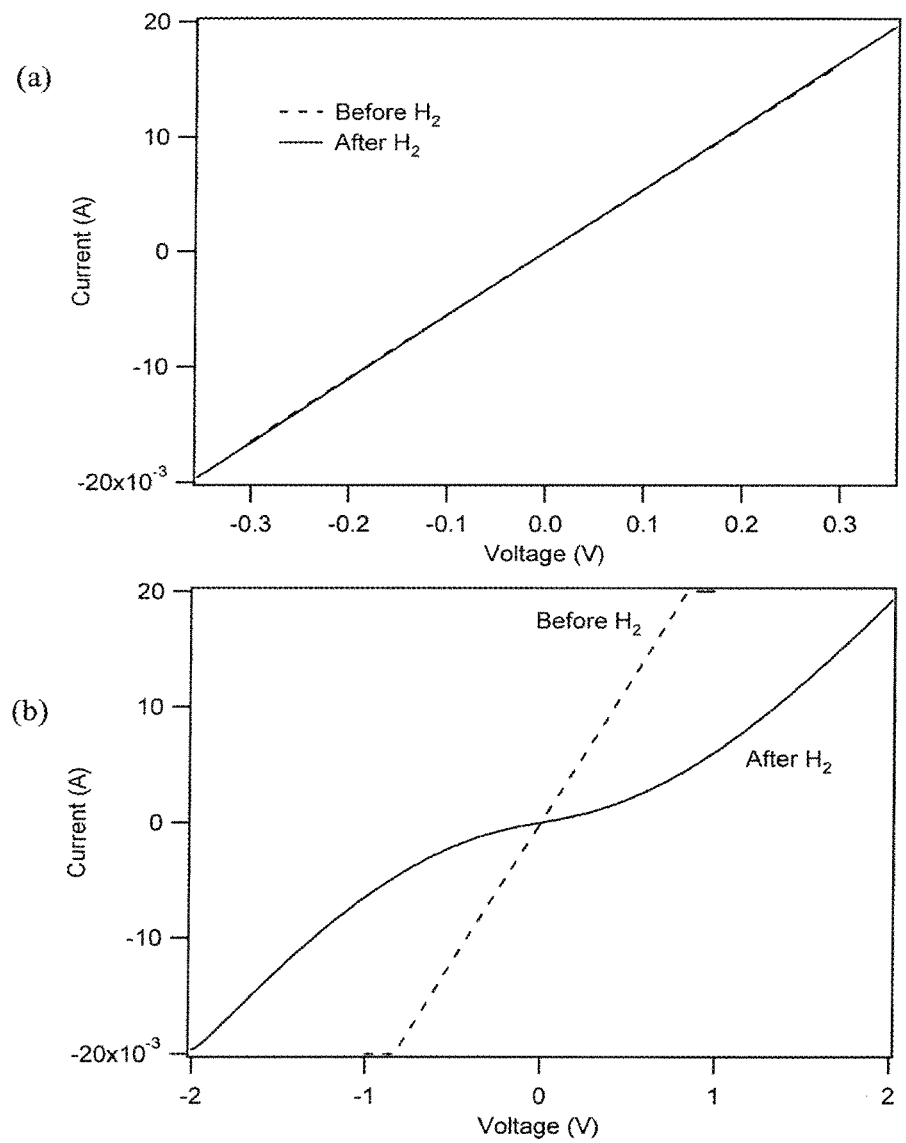
FIG. 15 shows IV curves of camphorsulfonic acid (CSA) doped polyaniline nanofibers deposited on a) gold electrodes and b) platinum electrodes before ( - - - ) and after (-) exposure to 1 percent hydrogen in a dry environment.
Figure 16:
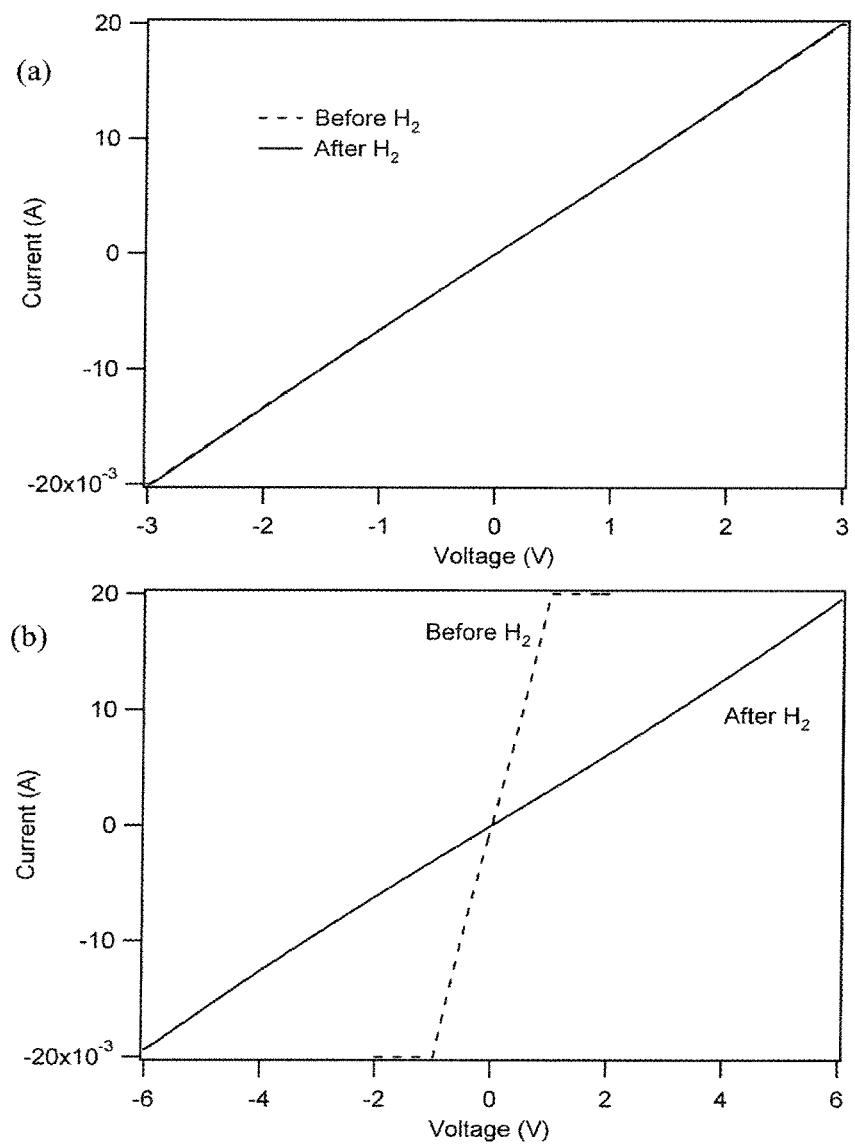
FIG. 16 shows IV curves of camphorsulfonic acid (CSA) doped conventional polyaniline deposited on a) gold electrodes and b) platinum electrodes before ( - - - ) and after (-) exposure to 1 percent hydrogen in a dry environment.

FIG. 15 shows IV curves of camphorsulfonic acid (CSA) doped polyaniline nanofibers deposited on a) gold electrodes and b) platinum electrodes before ( - - - ) and after (-) exposure to 1 percent hydrogen in a dry environment. FIG. 16 shows IV curves of camphorsulfonic acid (CSA) doped conventional polyaniline deposited on a) gold electrodes and b) platinum electrodes before ( - - - ) and after (-) exposure to 1 percent hydrogen in a dry environment. As can be seen, nonlinear behavior is exhibited for CSA doped polyaniline nanofibers deposited on platinum electrodes after exposure to hydrogen in a dry environment.

Table 1 (below) shows observed polyaniline nanofiber and conventional polyaniline film resistances on gold and platinum electrodes. The materials listed are CSA synthesized, CSA doped (CSA/CSA), $HNO_3$ synthesized, $HNO_3$ doped ($HNO_3/HNO_3$), $HNO_3$ synthesized and CSA doped ($HNO_3$/CSA) and conventional polyaniline.

TABLE 1

| Material | Film Resistance on Gold Electrodes ($\Omega$) | Film Resistance on Platinum Electrodes ($\Omega$) | $R_{Pt}/R_{Au}$ |
|---|---|---|---|
| CSA/CSA | 15 | 143.5 | 9.57 |
| $HNO_3/HNO_3$ | 55.5 | 162.5 | 2.93 |
| $HNO_3$/CSA | 29 | 319.5 | 11.0 |
| Conventional Polyaniline | 152 | 407 | 2.68 |

CONCLUSIONS

Camphorsulfonic acid doped polyaniline nanofibers interact with hydrogen to enhance charge transfer resulting in an observed resistance decrease in thin films. Dedoped polyaniline nanofiber films exhibit no significant interaction with hydrogen, especially in relation to the large and reversible response of doped films. The response of camphorsulfonic acid doped polyaniline nanofibers increases monotonically with hydrogen concentration. Humidity suppresses the hydrogen signal likely due to a competing interaction of water with hydrogen at the amine nitrogens on the polyaniline chain. Oxygen does not interfere with the interaction of hydrogen with polyaniline. An isotope effect is observed when comparing the response of hydrogen and deuterium with the hydrogen response being about 4 times larger than the deuterium response. Hydrogen mass uptake is observed using QCM sensors which also show a comparable deuterium isotope effect. When comparing conventional and nanofiber polyaniline films, there is a large enhancement of the response for the nanofiber polyaniline film due to better interaction of the gas with the small diameters and high surface area of the nanofibers.

These results suggest that polyaniline nanofibers have the potential of being a good room temperature hydrogen sensor in a dry atmosphere. The response is not inhibited by oxygen unlike many hydrogen sensors. Because humidity suppresses the hydrogen response, this sensor cannot be used directly in a humid atmosphere without a method to remove humidity.

These data clearly show that there is a hydrogen interaction with camphorsulfonic acid doped polyaniline nanofibers. This is interesting from both fundamental and applied perspectives. The confirmation of a significant interaction between hydrogen and polyaniline is important because this is a new type of interaction between hydrogen and a conducting polymer. The data indicate that polyaniline nanofibers do have some capacity to uptake hydrogen and additional hydrogen storage measurements are required to confirm this.

Although the present invention has been described in terms of the example embodiments above, numerous modifications and/or additions to the above-described embodiments would be readily apparent to one skilled in the art. It is intended that the scope of the present invention extend to all such modifications and/or additions.

What is claimed is:

1. A method for determining the quantity of molecular hydrogen ($H_2$) in a gas, comprising:
   providing a transduction device with a sensing layer consisting of polyaniline nanofibers in an acid-doped emeraldine salt form;
   the acid-doped emeraldine salt polyaniline nanofibers deposited on an between underlying electrodes to form an electrically conductive path between said electodes,
   wherein the acid-doped emeraldine salt polyaniline nanofibers are formed by doping polyaninline nanofibers with camphorsulfonic acid, sulfuric acid, nitric acid or polymeric acid dopants,
   said transduction device configured for measuring changes in electrical conductivity of the sensing layer caused by an interaction of the molecular hydrogen with the acid-doped emeraldine salt polyaniline nanofibers,
   measuring the electrical conductivity of the transduction device prior to exposure to the gas containing molecular hydrogen,
   exposing the transduction device sensing layer to the gas containing molecular hydrogen, said exposure to molecular hydrogen resulting in a reduced conductivity, the reduction in conductivity dependent on the concentration of the molecular hydrogen in the gas, and
   measuring the electrical conductivity of the transduction device following exposure to the molecular hydrogen and comparing the measurements both before and after exposure, said reduced conductivity thereof providing a measure of an amount of molecular hydrogen in the gas.

2. The method of claim 1, wherein the electrodes are made of platinum, said platinum and polyaniline nanofibers providing a nonlinear relationship between a measured conductivity change and the amount of hydrogen in the gas.

3. The method of claim 1 wherein the electrodes are interdigitated.

4. The method of claim 1, further including:
   providing a flow cell adjacent to the acid-doped emeraldine salt polyaniline nanofibers, and
   introducing the hydrogen containing gas to the flow cell.

5. The method of claim 4, wherein the apparatus is adapted to function with the flow cell at room temperature.

6. The method of claim 4 wherein the apparatus is adapted to maintain a dry atmosphere within the flow cell.

7. The method of claim 1, wherein the amount of hydrogen is presented as a hydrogen concentration.

8. The method of claim 1, wherein the acid-doped emeraldine salt polyaniline nanofibers are formed by doping polyaninline nanofibers with polymeric acid dopants.

9. The method of claim 1 wherein the polyaniline nanofibers have metal nanoparticles incorporated in or integral with the surface thereof.

10. The method of claim 9 wherein the metal nanoparticles include gold, silver, platinum or palladium.

11. A method for sensing molecular hydrogen, comprising:
    contacting a hydrogen free gas with a sensor and measuring the conductivity of said sensor,
    contacting the sensor with a gas containing molecular hydrogen, said sensor including at least two spaced apart electrodes, wherein a film consisting of acid-doped polyaniline nanofibers on and between the electrodes provides an electrically conductive path between the electrodes,
    wherein the polyaninline nanofibers are doped with camphorsulfonic acid, sulfuring acid, nitric acid or polymeric acid dopants,
    measuring the conductivity of the sensor contacting the hydrogen in the gas, and
    comparing the conductivity of the gas without and with molecular hydrogen to provide a ratio thereof, said ratio dependent on the percent molecular hydrogen concentration.

12. The method of claim 11 comprising introducing the gas into a flow cell, said flow adjacent the polyaniline nanofibers of the sensor.

13. The method of claim 12, wherein the flow cell is at room temperature.

14. The method of claim 13, further wherein the atmosphere in the flow cell is dry.

15. The method claim 12 wherein the flow cell contains oxygen.

16. The method of claim 11, wherein the change in conductivity correlates to a hydrogen concentration.

17. The method of claim 11 comprising forming the electrodes of platinum, said platinum and polyaniline nanofibers providing a nonlinear relationship between the measured conductivity changes and the amount of hydrogen in the gas.

18. The method of claim 11 wherein the electrodes are made of platinum or gold.

19. The method of claim 11 wherein the electrodes are interdigitated.

20. The method of claim 11 wherein the polyaniline nanofibers comprise an emeraldine salt form of polyaniline.

21. The method of claim 11, wherein the polyaniline nanofibers are doped with polymeric acid dopants.

22. The method of claim 11 wherein the polyaniline nanofibers have metal nanoparticles incorporated in or integral with the surface thereof.

23. The method of claim 22 wherein the metal nanoparticles include gold, silver, platinum or palladium.

24. The method of claim 8, wherein the polymeric acid dopants are chosen from the group consisting of polystyrenesulfonic acid and polyacrylic acid.

25. The method of claim 21, wherein the polymeric acid dopants are chosen from the group consisting of polystyrenesulfonic acid (PSSA) and polyacrylic acid (PAA).

* * * * *